(12) United States Patent
Gabrižová

(10) Patent No.: US 7,622,459 B2
(45) Date of Patent: Nov. 24, 2009

(54) METHOD OF PREPARATION OF A FUNGAL GLUCANE HYDROGEL HAVING ANTIBACTERIAL AND IMMUNOSTIMULANT ACTIVITY, AND USE THEREOF

(75) Inventor: Leona Gabrižová, Bratislava (SK)

(73) Assignee: Pleuran SRO, Bratislava (SK)

( * ) Notice: Subject to any disclaimer, the term of this patent is extended or adjusted under 35 U.S.C. 154(b) by 259 days.

(21) Appl. No.: 10/596,970

(22) PCT Filed: Jan. 4, 2005

(86) PCT No.: PCT/SK2005/000001

§ 371 (c)(1),
(2), (4) Date: Jun. 30, 2006

(87) PCT Pub. No.: WO2005/067977

PCT Pub. Date: Jul. 28, 2005

(65) Prior Publication Data

US 2007/0066563 A1 Mar. 22, 2007

(30) Foreign Application Priority Data

Jan. 14, 2004 (SK) .................... 34-2004

(51) Int. Cl.
*A01N 65/00* (2009.01)
*A61K 31/715* (2006.01)
*A01N 43/04* (2006.01)
*C12P 1/02* (2006.01)
*C12N 1/00* (2006.01)

(52) U.S. Cl. ............... 514/65; 514/54; 514/57; 435/171; 435/254.1; 435/255.1

(58) Field of Classification Search ........... 514/65, 514/54, 57; 435/254.1, 255.1, 171
See application file for complete search history.

(56) References Cited

U.S. PATENT DOCUMENTS

| 4,774,093 A | 9/1988 | Provonchee et al. |
| 5,158,772 A | 10/1992 | Davis |
| 6,444,448 B1 * | 9/2002 | Wheatcroft et al. ......... 435/101 |
| 2002/0192280 A1 * | 12/2002 | Hunter et al. ............... 424/465 |

FOREIGN PATENT DOCUMENTS

| EP | 0875244 | 11/1998 |
| WO | 9403500 | 2/1994 |
| WO | 02085950 | 10/2002 |

OTHER PUBLICATIONS

Brul, S., and Coote, P. Preservative agents in foods. Int. J. Food Microbiology 1999. 50 1-17.*

* cited by examiner

*Primary Examiner*—Sreeni Padmanabhan
*Assistant Examiner*—Sarah Pihonak
(74) *Attorney, Agent, or Firm*—Oppedahl Patent Law Firm LLC

(57) ABSTRACT

A method of preparation of a fungal glucane hydrogel having antibacterial and immunostimulant activity by alkaline deproteination and subsequent elimination of water-soluble components consists in that the obtained insoluble glucan is subsequently hydrated by wet grinding at a rotational speed of 3000 to 9000 rpm for 10 to 20 min. to a swelling volume in water of 50 to 500 ml/g. Then it is adjusted by heat sterilization at a temperature of 90 to 110° C. for 20 to 30 min., what results in a gel which is formed by fungal polysaccharide with the $\beta$-(1,3)-D-bond in the principal chain, with a concentration of 0.5 to 3% by weight. The fungal glucane hydrogel may be utilized for preparation of cosmetical, pharmaceutical and foodstuff products.

2 Claims, No Drawings

METHOD OF PREPARATION OF A FUNGAL GLUCANE HYDROGEL HAVING ANTIBACTERIAL AND IMMUNOSTIMULANT ACTIVITY, AND USE THEREOF

TECHNICAL FIELD

Present invention relates to a method of preparation of a fungal glucane hydrogel having antibacterial and immunostimulant activity, and to its use.

BACKGROUND ART

Some of the natural polysaccharides are characterized by immunostimulant and other pharmacological properties. The main carrier of the immunostimulant activity in natural polysaccharides are those polysaccharides, which have the β-(1,3)-D-glycosidic bond in the principal polysaccharide chain. It has been proven that immunoglucanes enhance immunity against various bacterial and virus diseases, they exhibit anticancer activity, potentiate the effect in radiotherapy and chemotherapy of of oncological patients.

Immunostimulant polysaccharides exist in cell walls of bacteria, yeasts and several fungi, especially of the *Basidiomycetes* genus. Immunopharmacologically active substances, to which the β-(1,3)-D-glycanes belong, are able to nonspecifically modify an extensive set of bacterial, fungal, parasitical and virus diseases. The mechanism of glucan action differs considerably from that of chemotherapeutics and antibiotics.

An immunostimulant glucan is according to the SK patent No. 282870 isolated from fruiting bodies of oyster mushroom, preferably from its stems by defibering, subsequent bleaching with hydrogen peroxide at a temperature of 15 to 25° C. for 15 to 24 hours in a medium of sodium hydroxide solution. The defibering is performed within 26 hours after picking the oyster mushrooms, which are stored at a temperature of 4 to 8° C., in a medium of an at least double amount of aqueous sodium or potassium carbonate solution with a concentration of 0.05 to 0.15% by weight, pH of the solution being 8 to 9, for 1 to 8 minutes. This results in a reaction suspension with the enzymatic activity of the present β-(1,3)-D-glucanase eliminated. From this suspension glucan is obtained by filtration and thorough washing. The glucan is then squeezed, dehydrated with ethanol and dried.

The aim of the present invention is recovery of glucan in the form of hydrogel, which is more active then the so far prepared glucan in the form of a powder.

DISCLOSURE OF INVENTION

The subject-matter of preparation of fungal glucan hydrogel having antibacterial and immunostimulant activity by alkaline deproteination and subsequent elimination of water-soluble components consists in that the so obtained insoluble glucan is subsequently hydrated by wet grinding at a rotational speed of 3000 to 9000 rpm for 10 to 20 min. to a swelling volume of 50 to 500 ml/g. The mixture prepared in this way is adjusted in the form of gel by heat sterilization at a temperature of 90 to 110° C. for 20 to 30 min., what results in a fungal polysaccharide with the β-(1,3)-D-bond in the principal chain, with a concentration of 0.5 to 3% by weight. If the so prepared hydrogel is used immediately after preparation, it needs not to be sterilized. However, in the case of longer storage it is chemically sterilized by addition of 0.02% of benzoic acid.

An aqueous solution of fungal glucan hydrogel is tasteless and odourless, it contains in ash at most 1.0% of nitrogen, at most 1.7% of sulfur, and according to the Foodstuff Code it is microbiologically harmless.

The fungal glucan hydrogel may be used for preparation of cosmetic formulations, where auxiliary substances forming hydrophilic ointment base are added to the fungal glucan hydrogel. Among the cosmetic formulations there are preparations for acne treating, for regeneration of skin, which is ageing, damaged by solar radiation and extremely stressed.

For pharmaceutical purposes it is used at various, including more serious skin injuries, like crus ulcers, eczema, inflammations, decubiti treating, and for accelerating of wounds and scars healing after surgical intervention, because the fungal glucan hydrogel is, besides having immunostimulant properties, also very well applicable to the skin.

The fungal glucan hydrogel is also suitable for preparation of food products, like yoghurts, curdy spreads, nutritional supplements for children, as it enhances immunity of the human organism.

EXAMPLES OF EMBODIMENTS

Example 1

100 g of glucane, prepared from fruiting bodies of oyster mushroom (*Pleurotus ostreatus*) is hydrated in a high-speed mixer in 5 l of water for 20 minutes at the rotational speed of 6000 rpm. Under these conditions, glucan is hydrated to the swelling volume in water of 250 ml/g, and the resulting viscous gel is subsequently heat sterilized at a temperature of 110° C. for 20 min.

Example 2

5 kg of fungal glucan hydrogel, prepared according to Example 1, is homogenized in a homogenizer with 10 kg of ointment base AMBIDERMAN, with addition of chemosterilant, N-cetyl-N,N,N-trimethylammonium bromide, in an amount of 0.1%, referred to the weight of the resulting cream, suitable for dermal applications at various diagnoses of skin diseases or to surgical wounds and skin defects.

Example 3

1 kg of fungal glucan is hydrated in 50 l of water in a high-speed mixer for 30 minutes at the rotational speed of 6000 rpm. Then 200 g of citric acid, 40 g of benzoic acid and 40 kg of fructose are added and it is sterilized at a temperature of 110° C. for 20 min. After sterilization 50 l of sterile water are added, in which 1 kg of —Ca-ascorbate has been dissolved. After homogenization of both components microbially stabilized syrup is obtained and filled in 100 ml glass vials.

The resulting syrup contains 10 mg of glucan hydrogel in 1 ml of syrup. The product is suitable especially for children in prophylactic and therapeutic treatment against various children's diseases.

Example 4

The glucan hydrogel in an amount of 100 mg/l is fed in a 1000 l tank with milk before milk sterilization. After sterilization and cooling the glucan hydrogel is inoculated with yoghurt culture in a regular technological process. The yoghurt produced contains 10 mg of immunoglucan in 100 ml of yoghurt. It is suitable especially for infant food and gerontologic population.

INDUSTRIAL APPLICABILITY

The fungal glucan hydrogel is suitable for preparation of products having antibacterial and immunostimulant properties in foodstuff and pharmaceutical industry. It is also suitable for preparation of creams for various purposes in cosmetic industry, as it exhibits good application properties.

The invention claimed is:

1. A method of preparing a fungal glucane hydrogel having antibacterial and immunostimulant activity, by the following steps:
  1. alkaline deproteination of fruiting bodies of oyster mushroom (*Pleurotus ostreatus*);
  2. subsequent elimination of water soluble components to obtain insoluble glucane;
  3. followed by hydration and defibration of the insoluble glucane by wet grinding, wherein the wet grinding is carried out at a rotational speed of 3000-9000 rpm for 10-20 minutes and to a swelling volume in water of 50 to 500 ml/g.;
  4. followed by heat sterilization at a temperature of 90 to 110° C. for 20 to 30 minutes, resulting in the hydrogel which is formed by the fungal polysaccharide from the fruiting body of *Pleurotus ostreatus*, with the β-(1,3)-D-glycosidic bond in the principal chain, in a concentration of 0.5 to 3% by weight.

2. The method according to claim 1, characterized in that the resulting gel is formed by fungal polysaccharide with the β-(1,3)-D-bond branched at every fourth anhydroglucose unit.

\* \* \* \* \*

UNITED STATES PATENT AND TRADEMARK OFFICE
CERTIFICATE OF CORRECTION

PATENT NO.      : 7,622,459 B2
APPLICATION NO. : 10/596970
DATED           : November 24, 2009
INVENTOR(S)     : Leona Gabrižová

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 392 days.

Signed and Sealed this

Twenty-sixth Day of October, 2010

David J. Kappos
*Director of the United States Patent and Trademark Office*